(12) United States Patent
Wellings (10) Patent No.: US 10,500,140 B2
(45) Date of Patent: Dec. 10, 2019

(54) MICROPARTICLE COMPOSITION AND USE THEREOF

(71) Applicant: Spheritech Ltd., Runcorn, Cheshire (GB)

(72) Inventor: Donald A. Wellings, Runcorn (GB)

(73) Assignee: Spheritech Ltd., Runcorn, Cheshire (GB)

( * ) Notice: Subject to any disclaimer, the term of this patent is extended or adjusted under 35 U.S.C. 154(b) by 0 days.

(21) Appl. No.: 16/330,171

(22) PCT Filed: Sep. 5, 2017

(86) PCT No.: PCT/EP2017/072268
§ 371 (c)(1),
(2) Date: Mar. 4, 2019

(87) PCT Pub. No.: WO2018/042058
PCT Pub. Date: Mar. 8, 2018

(65) Prior Publication Data
US 2019/0216691 A1    Jul. 18, 2019

(30) Foreign Application Priority Data
Sep. 5, 2016   (GB) .................................. 1615047.6

(51) Int. Cl.
*A61K 8/02* (2006.01)
*C11D 3/30* (2006.01)
(Continued)

(52) U.S. Cl.
CPC .......... *A61K 8/0245* (2013.01); *A61K 8/0241* (2013.01); *A61K 8/0275* (2013.01);
(Continued)

(58) Field of Classification Search
CPC ........ A61K 8/0245; A61K 8/368; A61K 8/49; A61K 8/4926; A61K 8/4946;
(Continued)

(56) References Cited

U.S. PATENT DOCUMENTS

2010/0278883 A1    11/2010   Liebmann et al.
2015/0151974 A1    6/2015    Lee et al.

FOREIGN PATENT DOCUMENTS

CN    102675568 A    9/2012
EP    0379409 A1     7/1990
(Continued)

OTHER PUBLICATIONS

UK Search Report, counterpart GB Appl. No. GB1615047.6, dated Jun. 29, 2017, 5 pages.
(Continued)

*Primary Examiner* — Trevor Love
(74) *Attorney, Agent, or Firm* — Cook Alex Ltd.

(57) ABSTRACT

The invention provides a personal care product or a home care product having self-assembled microparticles having an acid having two or more acid groups and an organic base in a solvent. The microparticles may form into a macrostructure and provide a support for carrying components of a personal care or home care composition. The particle is of micron scale. The microparticle may be obtained by contacting a bis-acid and organic base in a hydrophilic solvent, wherein the acid is insoluble or sparingly soluble in the hydrophilic solvent and the organic base is soluble in a hydrophilic solvent.

7 Claims, 6 Drawing Sheets

Brassylic acid microspheres (not cross-linked)

(51) Int. Cl.
*C11D 3/28* (2006.01)
*A61K 8/368* (2006.01)
*A61K 8/49* (2006.01)
*C11D 3/20* (2006.01)
*C11D 17/06* (2006.01)
*A61K 8/88* (2006.01)
*A61Q 19/00* (2006.01)
*A61Q 17/00* (2006.01)
*A61K 8/64* (2006.01)
*A61K 8/41* (2006.01)
*A61K 8/362* (2006.01)
*C08G 69/10* (2006.01)

(52) U.S. Cl.
CPC ............ *A61K 8/0279* (2013.01); *A61K 8/362* (2013.01); *A61K 8/368* (2013.01); *A61K 8/41* (2013.01); *A61K 8/49* (2013.01); *A61K 8/4926* (2013.01); *A61K 8/4946* (2013.01); *A61K 8/64* (2013.01); *A61K 8/88* (2013.01); *A61Q 17/005* (2013.01); *A61Q 19/00* (2013.01); *C11D 3/2082* (2013.01); *C11D 3/28* (2013.01); *C11D 3/30* (2013.01); *C11D 17/06* (2013.01); *C08G 69/10* (2013.01)

(58) Field of Classification Search
CPC .. A61K 8/0279; A61K 8/0275; A61K 8/0241; A61K 8/88; A61K 8/64; A61K 8/41; A61K 8/362; C11D 3/30; C11D 3/28; C11D 17/06; C11D 3/2082; A61Q 19/00; A61Q 17/005; C08G 69/10
See application file for complete search history.

(56) References Cited

FOREIGN PATENT DOCUMENTS

| | | |
|---|---|---|
| EP | 1398073 A1 | 3/2004 |
| GB | 2538139 A | 9/2016 |
| JP | 2010031197 A | 2/2010 |
| WO | WO2005/000258 A1 | 1/2005 |
| WO | WO2012/143508 A1 | 10/2012 |
| WO | WO2016/139322 A1 | 9/2016 |

OTHER PUBLICATIONS

International Search Report and Written Opinion, counterpart International PCT Appl. No. PCT/EP2017/072268, dated Oct. 30, 2017, 14 pages.

Figure 1:
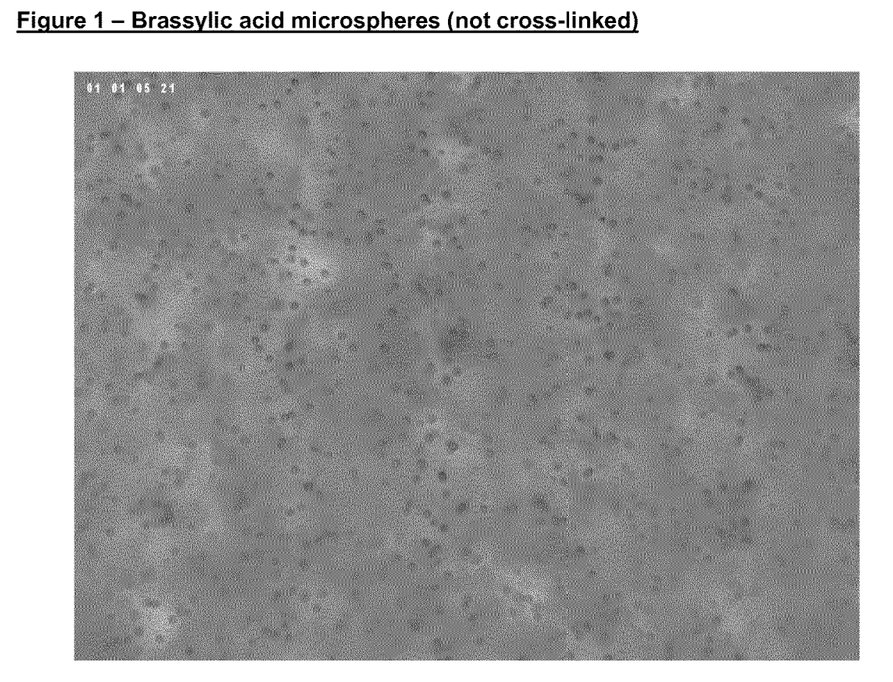

Figure 1 – Brassylic acid microspheres (not cross-linked)

Figure 2:
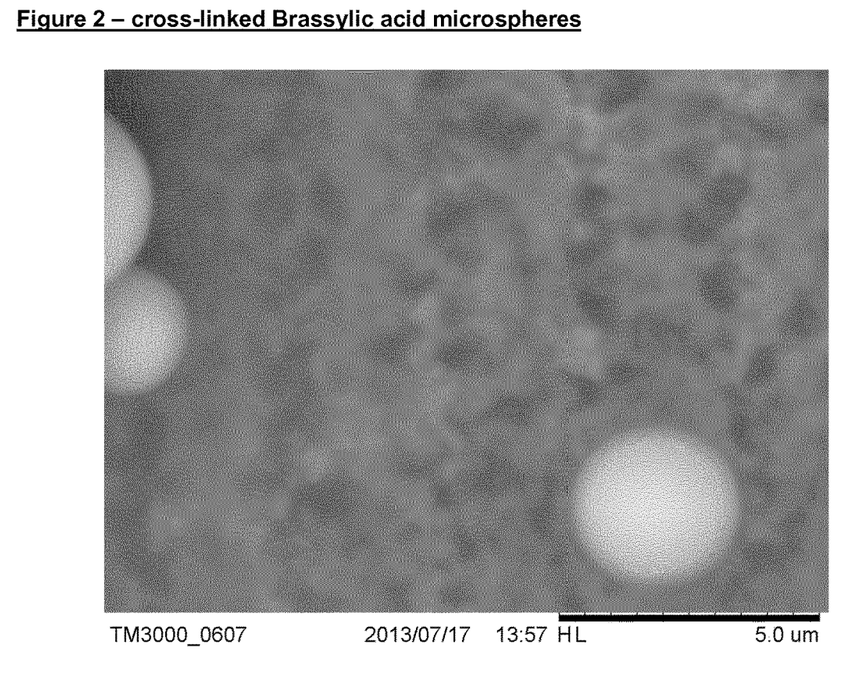

Figure 2 – cross-linked Brassylic acid microspheres

Figure 3:
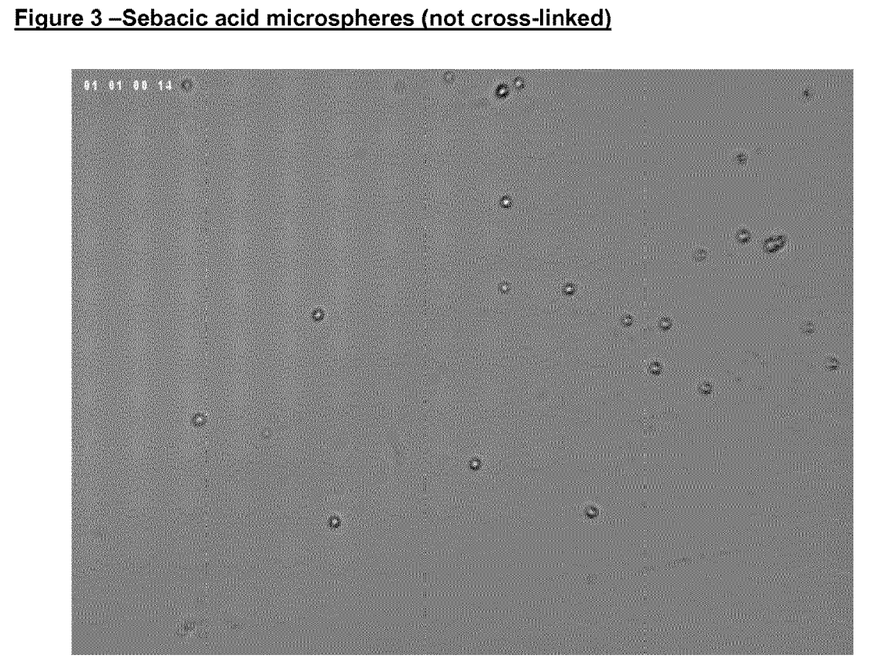

Figure 3 –Sebacic acid microspheres (not cross-linked)

Figure 4:
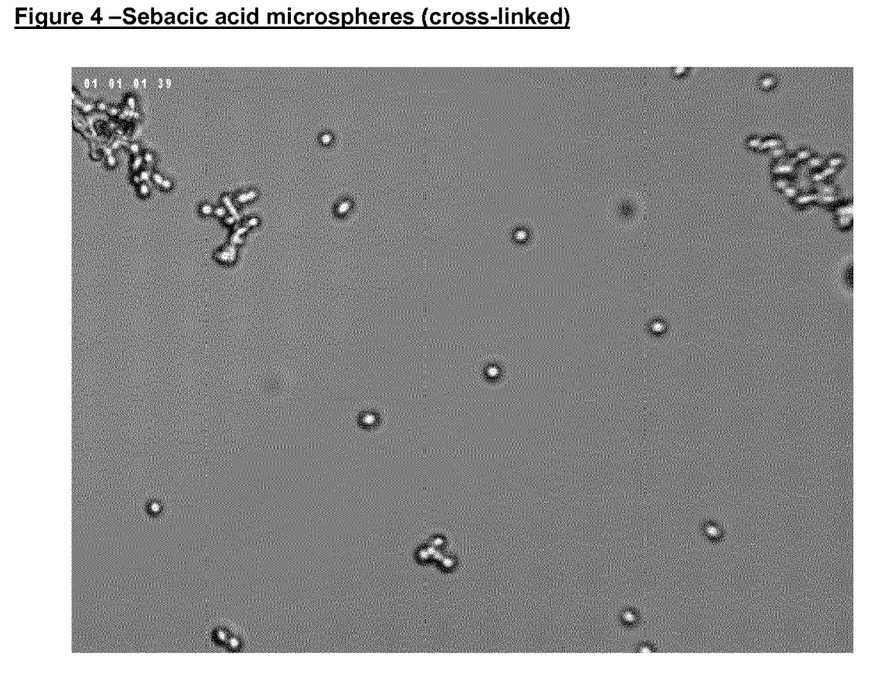

Figure 4 –Sebacic acid microspheres (cross-linked)

Figure 5:
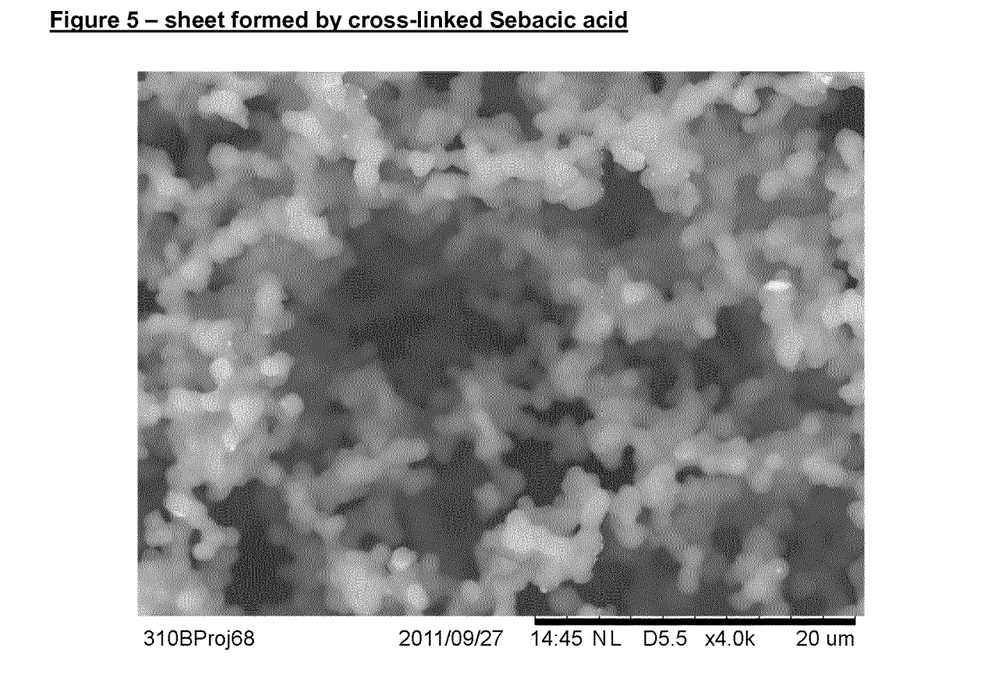
Figure 6:
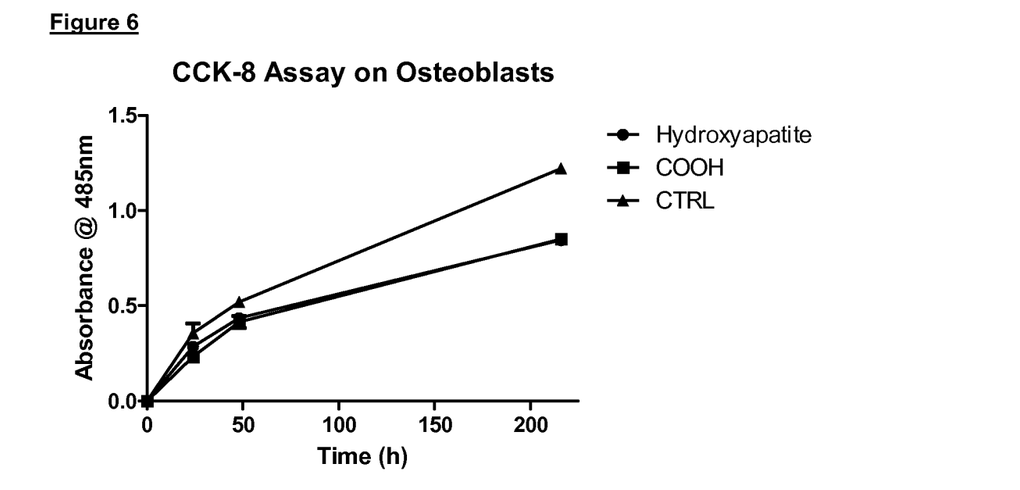
Figure 7:
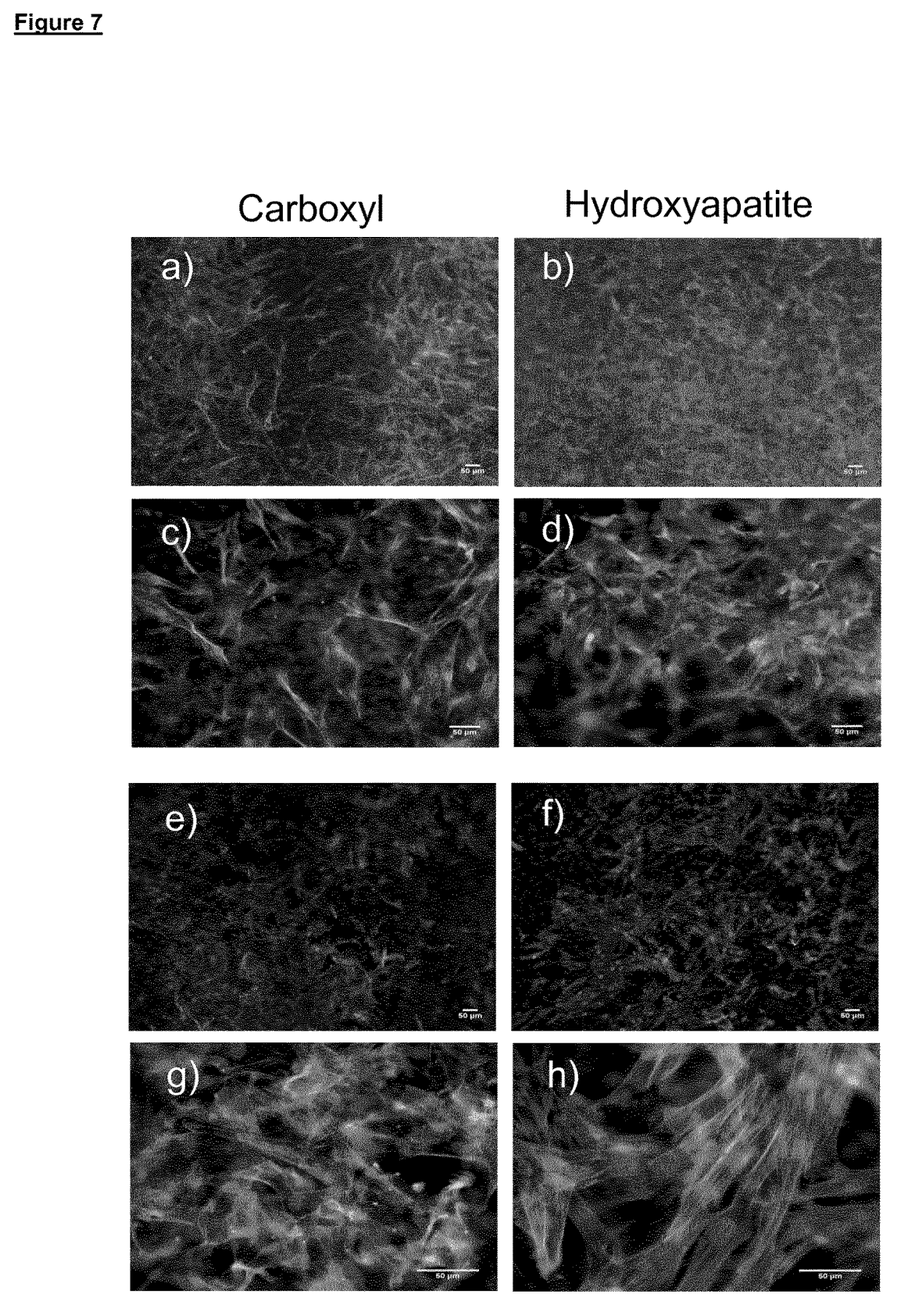

Figure 5 – sheet formed by cross-linked Sebacic acid

MICROPARTICLE COMPOSITION AND USE THEREOF

This invention relates to microparticle compositions and their use in personal care and home care compositions, in particular to microparticle compositions comprising self-assembled biodegradable microparticles and their use, a method of preparing the microparticle compositions, products comprising macroporous materials formed from said microparticles particles and their use.

The microparticle compositions and macroporous materials are useful in a wide range of processes especially where interaction with a substrate is required, for example a surface, an article, for example a fabric, a human or animal surface such as the skin and scalp. The compositions are especially useful as personal care products including skin creams and cosmetics, fragrances, deodorants, wipes, hand washes, shampoos, mouth washes and tooth pastes, and especially useful as home care products including surface treatments such as sprays and wipes, detergent compositions fabric softeners, fragrances, and dishwashing products.

Microparticles find widespread use in a wide range of compositions including personal care products and home care products. Microparticles made of plastics, silica or sand, spherulites and cellulose are known and those made of plastics presently find more widespread use than other microparticles. Plastics microparticles, also known as microplastics, are environmentally undesirable due to their lack of biodegradability and passing into marine environments and being absorbed or ingested by organic species.

Microplastics cause considerable damage to micro-organisms in the seas and ultimately to the fish and mammals in the chain than feed upon them. Microplastics are now found in all the world's major oceans as well as in the guts of most marine species, including the seafood we eat. Due to the nature of microplastics, removal of the particles from the sea is not feasible. The challenge to reduce environmental damage was the subject of a policy conference in 2015, organised by the OSPAR Commission and supported by the Ministry of Infrastructure and the Environment of the Netherlands. The OSPAR Commission was set up by the 1992 OSPAR Convention for the Protection of the Marine Environment of the North-East Atlantic, which unified and updated the 1972 Oslo and 1974 Paris Conventions. It brings together the governments of Belgium, Denmark, Finland, France, Germany, Iceland, Ireland, Luxembourg, the Netherlands, Norway, Portugal, Spain, Sweden, Switzerland and the United Kingdom, together with the European Union. It was estimated in a Eunomia report published February 2016 that 2,400 to 8,600 tons of microplastics from personal care and cosmetic products enter the marine environment from Europe alone every year.

Microplastics also find widespread use in toothpastes and home care products, such as detergents for fabric washing and other uses, fabric conditioners, dishwashing products and the like.

Typically, personal care products and cosmetics contain a range of ingredients that provide benefits to the end user and include, by way of example, skin care products which provide healthcare benefits for example sun screens, anti-spot agents and agents to soothe cracked skin. They often also include antimicrobial components or ingredients providing combined benefits including, by way of example, vitamin C, nicotinamide, alpha-hydroxy acids (glycolic, lactic, tartaric, and citric acids), retinol, hyaluronic acid, and dimethylamino ethanol.

Particulate and porous materials are also used to immobilise biological macromolecules for medical and diagnostic applications. This includes immobilisation of proteins, monoclonal and polyclonal antibodies. Cell culture is commonly carried out on solid supports with specific surface characteristics and morphology. Immobilised enzymes can be employed and may find applications in cosmetics and personal care products. Similarly, immobilised enzymes already have applications in detergent systems.

Home care and personal care products containing environmentally undesirable microparticles or microplastics are accordingly undesirable. A need exists for compositions for use in personal care and home care which are biocompatible and biodegradable and desirably antimicrobial and have the capability to act as a carrier for a functional ingredient depending on the intended use.

The manufacture of known polymeric particles may also be disadvantageous. Known polymer particles typically may be made by a dispersion or emulsion polymerisation process in which a solution of monomers is dispersed in an immiscible solvent (continuous phase) prior to initiation of the polymerisation. The polymer particles formed are typically then filtered, washed and classified to isolate the required particle size distribution. The process may however be complex and costly and be limited by the need to use organic solvents. The term "polymer" as employed herein includes inorganic polymers, for example silica and organic polymers, for example polyamide.

These processes are disadvantageous in some respects including monomer loss to the continuous phase, generation of a range of particle sizes and the undesirable generation of fine particles during the polymerisation leads to laborious particle size classification, for example by sieving or air classification.

In addition to undesirable costs of manufacture and wastage during preparation certain disadvantages may arise with the physical properties of the known polymeric particles. Microporous polymeric particles are generally soft and may have poor mechanical robustness. In addition, the soft particles may be compressed undesirably and cause fouling, for example during filtration making removal from waste streams, for example prior to entering the aquatic environment.

We have now found that these and other problems associated with personal care products and homecare products may be ameliorated by providing a self-assembled microparticle comprising a fatty acid having two or more carboxylic acid groups and a base formed by contacting self-assembled microparticles.

In a first aspect, the invention provides a personal care product comprising a personal; care base composition and a particulate component comprising a self-assembled microparticle.

The personal care base composition is suitably selected from skin cream and cosmetics, fragrances, deodorants, wipes, hand washes, hand scrubs, shampoos, conditioners, oral dentrifices, for example mouth washes, tooth pastes chewing gums, lozenges, bioadhesive patches or strips are suitable for brushing and/or rinsing the surfaces of the oral cavity, and the like. The personal care product is suitably formulated as a product for topical or oral administration and may include known components to aid topical or oral delivery.

In a second aspect the invention provides a home care product comprising a home care base composition and a particulate component comprising a self-assembled microparticle.

The home care base composition is suitably selected from surface treatments such as sprays and wipes, detergent compositions fabric softeners, fragrances, and dishwashing products.

The term "personal care base composition" and "home care base composition" means a composition containing conventional components for use in the specified application which, in combination with the biodegradable microparticles or macroporous structure formed from the microparticles described herein, provides a product suitable for personal care use or home care use as appropriate.

Preferably the personal care base composition is substantially free from microplastics or other non-biodegradable microparticles. Preferably the home care base composition is substantially free from microplastics or other non-biodegradable microparticles.

Suitably the microparticle comprises an acid having two or more acid groups and an organic base which is soluble in a hydrophilic solvent. Preferably the acid comprises a bis-acid, preferably a bis-aliphatic acid and suitably comprises two or more carboxylic acid groups, although other acid groups may be employed. Suitably the bis-acid is insoluble or sparingly soluble in the hydrophilic solvent. Suitably, by contacting the acid, preferably bis-aliphatic acid with an organic base which is soluble in the hydrophilic solvent, the acid may be solubilised.

The solvent is suitably hydrophilic, preferably an aqueous solution, for example a water in oil emulsion within an aqueous phase, and especially water.

Advantageously, an aqueous-based solvent, preferably water, allows the microparticle to be used in applications in which environmental considerations are important.

Suitably the acid and base components of the microparticles comprise are cross-linked by amide bonds. Advantageously the microparticles are biodegradable by protease activity and aqueous hydrolysis and are accordingly environmentally beneficial. Suitably, other components may be carried by amide bond formation, or by simple ionic interactions, by hydrophilic, or by hydrophobic interactions.

The microparticles suitably have a narrow particle size distribution.

In the preferred embodiment the bis-aliphatic acid comprises a bis-carboxylic fatty acid in which terminal carboxylic acids are linked by a region which is less hydrophilic than the terminal carboxylic acids and is preferably hydrophobic. The less hydrophilic region may comprise a backbone with substituents and/or the backbone may comprise heteroatoms, for example poly-epsilon lysine. Preferably the region linking the carboxylic acids is hydrophobic and preferably a hydrocarbyl group. In an especially preferred embodiment, the hydrophobic group is an aliphatic hydrocarbyl group. Preferably, the bis-acid comprises a compound of general formula $HOOC-(CH_2)_n-COOH$ wherein n is sufficiently large that the bis acid is sparingly soluble or insoluble in water. Preferably n is at least 5, more preferably at least 6, especially at least 7. Suitably n is not more than 40, preferably not more than 36, more preferably not more than 25, and especially not more than 20. Preferably n is from 7 to 18.

In a preferred embodiment, the organic acid comprises a $C_7$ to $C_{18}$ bis carboxylic fatty acid. In another preferred embodiment, the organic acid comprises a $C_7$ to $C_{13}$ bis carboxylic fatty acid together with a further acid selected from a EDTA, nitrolotriacetic acid and a monocarboxylic acid, preferably a $C_6$ to $C_{18}$ carboxylic acid, for example caproic acid, palmitic acid and octanoic acid.

By selecting more than one acid for example in which the acids have different n values, the size of the microparticle may be tailored. A longer hydrophobic portion connecting the acid groups suitably provides a larger microparticle. For example where n is 8, sebacic acid, a particle of size 2.6 microns may be obtained and where n is 11, brassylic acid, a particle of size 3.0 microns may be obtained.

The bis-carboxy fatty acid can also be unsaturated for example traumatic acid, or substituted or both unsaturated and substituted. Suitably, the substitution does not cause the bis-acid to be soluble in aqueous solution. When the bis-aliphatic acid is contacted with the aid of a solvent soluble organic base, microparticles are formed spontaneously.

The bis-aliphatic acid may comprise: a bis-phosphonic acid of general formula $(HO)_2OP-(CH_2)_n-PO(OH)_2$ or an unsaturated bis-phosphonic acid; a mono-carboxylic mono-phosphonic acid of general formula $HOOC-(CH_2)_n-PO(OH)_2$ or an unsaturated version of such bis-acid; a bis-sulfonic acid of general formula $(HO)O_2S-(CH_2)_n-SO_2(OH)$ or an unsaturated version of such bis-acid; a mono-carboxylic mono-sulfonic acid of general formula $HOOC-(CH_2)_n-SO_2(OH)$ or an unsaturated version of such a bis-acid; a bis-boronic acid of general formula $(HO)_2B-(CH_2)_n-B(OH)_2$ or an unsaturated bis-boronic acid, or substituted bis-boronic acid; a mono-carboxylic mono-boronic acid of general formula $HOOC-(CH_2)_n-B(OH)_2$ an unsaturated version of such bis-acid; or a substituted version of said bis-acids. In these acids, n is sufficiently large that the bis acid is sparingly soluble or insoluble in water. Preferably n is at least 5, more preferably at least 6 and especially at least 7. Suitably n is not more than 40, preferably not more than 36 more preferably not more than 25, and especially not more than 20. Preferably n is from 7 to 18.

In formation of the microparticle or macroporous material the bis acid component may comprise more than one acid and in this case the bis-acids may be mixed in any proportions.

Suitably, the organic base combines with the bis-acid moieties such that the combination of the two components comprises two separate hydrophilic or ionic head regions connected by a hydrophobic region. Without wishing to be bound by theory, it is believed that the hydrophobic regions and hydrophilic regions of adjacent bis-acids with organic base align to form micelles and lead to self-assembly of the microparticles of the invention. Preferably, the microparticle comprises a multi-lamellar structure in which further molecules comprising the bis-acids with the organic base, align with the hydrophilic head of another bis-acid/organic base so as to form a multi-lamellar structure.

The organic base may be selected from a range of bases which, together with the bis-acid forms a self-assembling microparticle. Preferably, the organic base comprises an amine, suitably an aliphatic amine or an aromatic amine having a basic character or other nitrogen-containing base, a reactive amine or a polymeric amine.

Examples of suitable organic bases include alkylated amines and polyamines including amines having one or two $C_{1-4}$ N-alkyl-groups, for example methylated amines. Examples of preferred amines include N-methylmorpholine, 4-methylmorpholine (NMM), N,N-dimethylaminoethanol (DMAE), 4-dimethylaminopyridine (DMAP), imidazole or 1-methylamidazole, poly(diallyldimethylammonium chloride) (PDAC), didecyldimethylammonium chloride (DDAC) and dodecyldipropylenetriamine (DDPT).

The amine-containing organic component may be a reactive amine or a polymeric amine including but not limited to a peptide, protein, polyallylamine, polyethyleneimine.

Examples of suitable reactive amines and polyamines include ethylenediamine, poly-e-lysine, polyallylamine, polyethyleneimine, aminopropyltrialkoxysilanes, 3-(2-aminoethylamino)propyltrimethoxysilane, N-(3-(trimethoxysilyl)-propyl)diethyenetriamine.

The organic base component may comprise more than one base and in this case the organic bases may be mixed in any proportions.

In preferred embodiments, the acid is suitably one or more of brassylic acid, sebacic acid and azelaic acid in combination with a base selected from methylmorpholine (NMM), N,N-dimethylaminoethanol (DMAE), 4-dimethylaminopyridine (DMAP), imidazole, 1-methylamidazole, poly(diallyldimethylammonium chloride) (PDAC), didecyldimethylammonium chloride (DDAC) and dodecyldipropylenetriamine (DDPT).

Examples of preferred embodiments include microparticles comprising brassylic acid and PDAC, brassylic acid and DDAC, brassylic acid and DDPT, sebacic acid and NMM, poly epsilon lysine in combination with one or more of sebacic acid, brassylic acid and azelaic acid.

We have found that microparticles employed in personal care products or home care products according to the invention comprising amines having antimicrobial properties are particularly suited for use as antimicrobial compositions and biocides. The level of antimicrobial activity of the base may be higher when in the form of a self-assembled microparticle according to the invention as compared to when in a conventional formulation.

According to a further aspect the invention provides an antimicrobial personal care composition comprising a personal care base composition as described herein and a self-assembled microparticle comprising a bis acid and an antimicrobial base.

According to another aspect, the invention provides an antimicrobial home care composition comprising a home care base composition as described herein and self-assembled microparticle comprising a bis acid and an antimicrobial base.

The invention also provides the use of a self-assembled microparticle comprising a bis acid and an antimicrobial base having a higher level of antimicrobial activity than the antimicrobial base when not in the form of a self-assembled microparticle.

Suitably, providing the antimicrobial base in a self-assembled microparticle increases the antimicrobial activity and provides at least a 2 log reduction of bacterial load, preferably at least a 4 log reduction of bacterial load and desirably at least a 5 log reduction of bacterial load.

The acid and base are suitably combined in relative quantities such that the molar ratio of acid groups in the acid to basic groups in the base is approximately stoichiometriuc such that self-assembled microparticles form. The molar quantity of acid groups to base groups may be less or more than stoichiometric provided the self-assembled particles form. Where the ratio of acid groups to base groups is too low or too high, -assembled particles do not form as the excess component disrupts structure of the acid and base. The ratio of acid groups to basic groups that allow formation of the self-assembled particle will vary depending on the particular acid and particular base.

The skilled person will be able to determine whether a self-assembled particle is formed by observing under a microscope with magnification at a level to visually observe particles for example at 40× magnification. The relative quantities of the acid and base will be able to be modified to determine the minimum and maximum ratio of the components at which microparticles form. Acids having longer chains may provide microparticles which are more stable than microparticles (with the same base and same molar ratio) comprising an acid having a shorter chain. The greater stability may allow a lower level of acid to be employed and a lower ratio of acid groups to basic groups may still allow a microparticle to form.

Suitably, the ratio of acid groups to basic groups in the acid and base is from 0.6 to 1.4:1, preferably 0.7 to 1.3:1, more preferably 0.8 to 1.2:1 and desirably 0.9 to 1.1:1. Sebacic acid and brassylic acid are examples of preferred acids. Suitably a microparticle comprising sebacic acid with a base has a ratio of sebacic acid to base of 0.85 to 1.15:1. A microparticle comprising brassylic acid with a base has a ratio of brassylic acid to base of 0.8 to 1.2:1. In a preferred embodiment, the acid and base are present at levels to provide a molar ratio of acid groups to basic groups of 1:1.

In another aspect, the invention provides a personal care product comprising a personal care base composition as described herein and a macroporous material formed by contacting self-assembled microparticles under conditions such as to form a macroporous material.

According to another aspect, the invention provides an antimicrobial home care composition comprising a home care base composition as described herein and macroporous material formed by contacting self-assembled microparticles under conditions such as to form a macroporous material.

The macroporous material is suitably formed by cross-linking microparticles.

The organic base may be reactive so as to enable cross-linking of the self-assembled microparticles for form a macroporous material. The organic base need not be reactive in which case it may suitably be displaced by another reactive species to allow subsequent cross-linking to form a macroporous material. The solvent soluble organic base can be displaced by addition of a reactive species including, but not limited to, amine containing organic components. The amine suitably allows cross-linking of the microparticles by amide bond formation. In the preferred embodiment the amine containing organic component is a polymeric amine including but not limited to a peptide, protein, polyallylamine, polyethyleneimine and other polyamines.

Examples of suitable amines and polyamines include ethylenediamine, poly-e-lysine, polyallylamine, polyethyleneimine, aminopropyltrialkoxysilanes, 3-(2-aminoethylamino) propyltrimethoxysilane, N-(3-(trimethoxysilyl)-propyl)diethyenetriamine.

In formation of the microparticle or macroporous material the above aforementioned bis acids may be mixed in any proportions. In addition, the reactive amines may also be mixed.

Suitably, the microparticles or macroporous materials comprises functional components, tailored according to the intended use. For example the addition of ethylenediamine tetra acetic acid imparts metal chelating properties.

In another embodiment, polyethylene imines may be employed in binding or as a support structure.

Alkoxysilanes may be employed and may form a silica shell in the lamellar layers of the microparticle.

In another embodiment the active site of a specific enzyme can be incorporated into a peptide within the particles to allow for controlled release of an active agent. For example, the cleavage site of a wound based metallinoprotease could be incorporated in wound care based materials to allow controlled release of an antibacterial agent.

In another application, the microparticles of the invention may be employed to form a macrostructure for the growth cells.

A self-assembled microparticle or macroporous material according to the invention may also comprise a functional material supported by the polymer. Examples of suitable functional materials include a pharmaceutical active, a macromolecule, an enzyme, a nucleic acid sequence and a protein.

In another embodiment the active site of a specific enzyme can be incorporated into a peptide within the particles to allow for controlled release of an active agent. For example, the cleavage site of a wound based metallinoprotease could be incorporated in personal care products which also provide controlled release of an antibacterial agent.

The invention provides in a further aspect a method for producing a self-assembled microparticle or macroporous material in aqueous media comprising contacting the two acid having two or more acid groups with an organic base in an aqueous medium, preferably water.

Suitably the polymerisation and cross-linking is initiated by processes known to those skilled in the art. For example, self-assembled microparticle or macroporous material prepared in water with an amine containing component can be cross-linked using a water soluble carbodiimide.

Suitably, the self-assembled microparticle or macroporous material is substantially mono-disperse. That is the material has particles which are all substantially the same size. That is the material has particles which are all substantially the same size. Monodisperse microparticles or macroporous materials can be advantageous, for example in controlled release of an agent. The agent could for example be a vitamin in cosmetic or personal care applications, or an enzyme in biological detergents.

The virtually monodispersed nature of the self-assembled microparticles in a preferred embodiment of the invention allows preparation of the slurry and transfer of the slurry to the column to form a more uniform mixture. Alternatively the macroporous material formed by collision of the self-assembled microparticle can be used to prepare a monolithic sheet which is suitable for use as a facial treatment or a wipe.

In another embodiment the interstitial spaces between the particles in a monolith may be filled with a different component such as a cosmetic treatment.

The self-assembled microparticles and macroporous material of the invention is especially useful in immobilising species including catalysts, bio-catalysts, enzymes, proteins, antibodies including polyclonal and monoclonal antibodies, whole cells and polymers. The invention is particularly advantageous in supporting enzymes, for example the lipase Cal B, commonly used in detergents and personal care products.

The personal care product or home care product according to the invention containing the self-assembled microparticles and/or macroporous material may be used as an absorbent product.

Suitably, the support contains an inert, absorbent material bound to the self-assembled microparticles and/or macroporous material. The self-assembled microparticles and/or macroporous material may be used to absorb household spillages, for example tea, coffee and wine. The absorbent support may be used to absorb the spillage and then physically removed or, in the case of oil spillage in a body of water, effectively trap the oil and retain the oil in a retained mass for collection and disposal.

The personal care product may be any product adapted for use in personal care of the human or animal body. The personal care base composition s suitably a liquid, lotion, cream, foam, scrub, gel, soap bar or toner, or applied with an implement or via a face mask, pad or patch.

The personal care base composition is preferably selected from a skin care composition, for example a skin cream, a cosmetic, a fragrance, a deodorant, a hand or a face wipe, a hand wash, a hand scrub, a skin-lightening composition, a shampoo, a conditioner, a mouth wash, a tooth paste and a tooth whitening agent.

The personal care base composition for use as a skin care product suitably comprises a cosmetically acceptable carrier. Examples of suitable carriers include water, emollients, fatty acids, fatty alcohols, humectants, thickeners and combinations thereof. The carrier may be aqueous, anhydrous or an emulsion. Preferably the compositions are aqueous, especially water and oil emulsions of the W/O or O/W or W/O/W type. Water when present may be in amounts ranging from about 5 to about 95%, preferably from about 20 to about 70%, optimally from about 35 to about 60% by weight.

Emollient materials may serve as cosmetically acceptable carriers. Examples of suitable emollients include silicone oils, synthetic esters and hydrocarbons. Preferably the emollient is present at a level of about 0.1 to about 95%, preferably between about 1 and about 50% by weight of the composition.

The personal care composition may also comprise a surfactant. Suitably, the surfactant is present at a level of about 0.1 to about 40%, preferably from about 1 to about 20%, optimally from about 1 to about 5% by weight of the composition. The surfactant may be selected from the group consisting of anionic, nonionic, cationic and amphoteric actives. Particularly preferred nonionic surfactants are those with a C10-C20 fatty alcohol or acid hydrophobe condensed with from 2 to 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan, mono- and di- C8-C20 fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, C8-C20 acyl isethionate, C8-C20 alkyl ether phosphates, C8-C20 sarcosinates and combinations thereof.

In a preferred embodiment, the personal care base composition comprises a vitamin, especially vitamin B3. Examples of vitamins include Vitamin A (retinol), Vitamin B2, Vitamin B3 (niacinamide), Vitamin B6, Vitamin B12, Vitamin C, Vitamin D, Vitamin E, Vitamin K and Biotin. Suitably the vitamin is present a t a level of from 0.0001 to 10%, preferably from 0.01% to 1%, optimally from 0.1 to 0.5% by weight of the composition.

Where the personal care base composition is an antiperspirant or deodorants, the base composition suitably comprises a metal salts of aluminum, zinc, zirconium and zirconium aluminum mixtures of sulfates, chlorides, chlorohydroxides, tetrachlorohydrex glycinates, alums, formates, lactates, benzyl sulfonates, succinates, phenol sulfonates and the like. Typical levels of antiperspirant/deodorant agent are from about 0% to about 35%, preferably from about 0% to about 25% by weight of the composition.

The deodorant or antiperspirant composition suitably comprises a conventional deodorant base as the cosmetically acceptable carrier and may comprise hydrophilic and/or hydrophobic components. Suitable hydrophobic liquid carriers include siloxanes, hydrocarbons, branched aliphatic alcohols, esters and ethers that have a melting point not higher than 25° C. and a boiling point of at least 100° C. Suitable hydrophilic carrier liquids include water and/or a mono- or polyhydric alcohol or water-miscible homologue.

For firm deodorants, the base composition may comprise waxes including materials of natural origin that are solid with a waxy feel and water-insoluble at 30-40° C., and melt at a somewhat higher temperature, typically between 50 and 95° C., such as beeswax, candelilla or carnauba wax. Other suitable waxes include hydrocarbon waxes, e.g. paraffin wax, mineral wax and microcrystalline wax; synthetic waxes, such as polyethylene of 2000 to 10000 daltons; waxy derivatives or waxy components of natural waxes.

The antiperspirant or deodorant base composition may be in the form of an aerosol composition and comprises a propellant in addition to the deodorant/anti-perspirant base composition.

Where the personal care product is a dentifrice, for example a toothpaste mouth wash or tooth whitening agent. A dentifrice is an oral composition that is not intentionally swallowed but is applied to the oral cavity, used to treat the oral cavity and then expectorated. Suitably the dentifrice is solid, semi-solid or liquid for example a paste or a gel.

The dentifrice base composition suitably comprises an aqueous continuous phase, suitably comprising a mixture of water and polyhydric alcohol in conventional amounts. Typical polyhydric alcohols for use in a dentifrice composition include humectants such as glycerol, sorbitol, polyethylene glycol, polypropylene glycol, propylene glycol, xylitol (and other edible polyhydric alcohols), hydrogenated partially hydrolyzed polysaccharides and mixtures thereof. The dentifrice may comprise an abrasive material for example a particulate calcium carbonate abrasive, an abrasive silica, other calcium sodium and potassium metaphosphate, sodium and potassium pyrophosphates, sodium trimetaphosphate, sodium hexametaphosphate, particulate hydroxyapatite and mixtures thereof. The dentifrice may contain a binders or thickening agent. The dentifrice may comprise a surfactant, suitably in an amount of from 0.2 to 5% by weight based on the total weight of the dentifrice.

The dentifrice may be a mouthwash being a liquid formulation used to rinse the surfaces of the oral cavity. A preferred A mouthwash base composition comprises a mixture of water and polyhydric alcohol in various relative amounts known in the art.

Further ingredients useful in skin care compositions herein may be selected from any and all: skin conditioning agents, skin feel mildness agents, suspending agents, auxiliary thickening agents, viscosity control agents, dispersants, solubilizing/clarifying agents, stabilizers, opacifiers/pearlescent agents, chelating/sequestering agents, hydrotropes, bactericides/fungicides, antioxidants, pH control agents, buffering agents, colorants and perfumes/fragrances, water, other optional ingredients (auxilary agents) and the like.

The compositions of the present invention can also be optionally, incorporated into a water insoluble substrate for application to the skin such as in the form of a treated wipe.

Where the personal care product is suitable for personal cleaning, the personal care base composition preferably comprises from 1 to 80% by weight of one or more surfactants and a carrier as described herein.

Any type of surfactant, i.e. anionic, cationic, nonionic, zwitterionic or amphoteric can be used. Preferably, the one or more surfactants are anionic, nonionic, or a combination of anionic and nonionic surfactants. More preferably, the one or more surfactants are anionic. Soap is a particularly preferred surfactant. Soap is especially a suitable surfactant for personal washing applications of the antimicrobial composition of the invention. The soap is preferably C8-C24 soap. The cation of the soap is suitably selected from sodium, potassium or ammonium.

Where the personal care product is for use in oral care for example in a dentifrice/toothpaste or an oral rinse product, the personal care base composition preferably comprises one or more anionic, nonionic or amphoteric surfactant. Suitable anionic surfactants include an alkali metal alkyl sulphate, more preferably a sodium lauryl sulphate (SLS). Suitable amphoteric surfactants include a betaine, more preferably an alkylamidopropyl betaine and especially a cocoamidopropyl betaine (CAPB). Suitable surfactant concentrations in oral care application are generally from about 2% to about 15%, preferably from about 2.2% to about 10%, more preferably from about 2.5 to about 5% by weight of the total composition.

The personal care base composition suitably comprises soap, alkyl sulphate or linear alkyl benzene sulphonate as a surfactants and a carrier, preferably water.

The home care base composition suitably comprises a surfactant and a carrier. Preferably the surfactant comprises one or more anionic, nonionic or amphoteric surfactants. Preferably the home care base composition comprises soap, alkyl sulphate or linear alkyl benzene sulphonate as a surfactants and a carrier, preferably water.

The home care base composition may be a detergent composition. Preferably the detergent composition comprises a surfactant as described above and a builder and optionally one or more of a bleach and an enzyme.

Where the home care base composition is a fabric conditioner, it suitably comprises a fabric softening compound, for example a quaternary ammonium salt.

The invention is illustrated by the following non-limiting examples.

EXAMPLE 1

Preparation of Self-assembled Microparticles

Brassylic acid (1.54 g, 6.31 mmol) and 4-dimethylaminopyridine (DMAP, 1.54 g, 12.62 mmol) were dissolved in water (10 cm$^3$) and a sample placed on a microscope. Almost monodispersed spherical entities of ~3 μm diameter were observed (FIG. 1).

EXAMPLE 2

Preparation of Self-assembled Microparticles

Brassylic acid (1.54 g, 6.31 mmol) and dimethylaminoethanol (DMAE, 1.12 g, 12.62 mmol) were dissolved in water (10 cm$^3$) and a sample placed on a microscope. Almost monodispersed spherical entities of ~3 μm diameter were observed.

EXAMPLE 3

Preparation of Self-assembled Microparticles

Brassylic acid (1.54 g, 6.31 mmol) and 4-methylmorpholine (NMM, 1.275 g, 12.62 mmol) were dissolved in water (10 cm³) and a sample placed on a microscope. Almost monodispersed spherical entities of ~3 µm diameter were observed.

EXAMPLE 4

Preparation of Self-assembled Microparticles

The above dicarboxylic acid dissolution experiments were also carried out using a range of acids and a range of water soluble organic bases. Some of the combinations tested are listed below. The combinations had an acid group to basic group molar ratio of 0.9 to 1.1:1. All of these combinations formed the spherical entities as described in EXAMPLE 1.
Pimelic acid plus NMM
Suberic acid plus NMM
Azelaic acid plus NMM
Sebacic acid plus NMM
Sebacic acid plus DMAP
Sebacic acid plus DMAE
Sebacic acid plus imidazole
Dodecanedioic acid plus NMM
Dodecanedioic acid plus DMAP
Dodecanedioic acid plus DMAE
C36 dimer acid plus NMM

EXAMPLE 5

Preparation of Cross-linked Self-assembled Microparticles

Brassylic acid (1.54 g, 6.31 mmol) and 4-dimethylaminopyridine (DMAP, 1.54 g, 12.62 mmol) were dissolved in water (10 cm³) and a sample placed on a microscope. Almost monodispersed spherical entities of ~3 µm diameter were observed (FIG. 1).
Poly-epsilon-lysine (PeK) (2 g, 12.04 mmol of $NH_2$) was dissolved in water (10 cm³) and added to the above solution of Brassylic acid/DMAP microspheres. The mixture was filtered through a 0.45 µm membrane and a sample placed on a microscope. Microspheres of ~3 µm diameter were still present. This solution was diluted with water to 100 cm³. N-(3-Dimethylaminopropyl)-N'-ethylcarbodiimide hydrochloride (EDCI)(4.6 g, 2.4 mmol) and HONSu (1.38 g, 1.2 mmol) were dissolved in water (10 cm³) and added to the above solution. The cross-linking reaction was left overnight, the resultant particles washed by tangential flow filtration (TFF) and recovered by lyophilisation (yield 2.35 g). FIG. 2 shows a scanning electron micrograph of the resultant microspheres.

EXAMPLE 6

Preparation of Cross-linked Self-assembled Microparticles Containing Protoporphyrin IX, Heme B Brassylic acid (0.734 g, 3.3 mmol) and 4-dimethylaminopyridine (DMAP, 0.734 g, 6.6 mmol) were dissolved in water (10 cm³) and a sample placed on a microscope. Almost monodispersed spherical entities of ~3 µm diameter were observed (FIG. 1).
Poly-epsilon-lysine (PeK) (1 g, 6.02 mmol of $NH_2$) was dissolved in water (10 cm³) and added to the above solution of Brassylic acid/DMAP microspheres. The mixture was filtered through a 0.45 µm membrane and a sample placed on a microscope. Microspheres of ~3 µm diameter were still present. This solution was diluted with a saturated solution of Heme B (50 cm³). N-(3-Dimethylaminopropyl)-N'-ethylcarbodiimide hydrochloride (EDCI)(2.3 g, 1.2 mmol) and HONSu (0.7 g, 0.6 mmol) were dissolved in water (5 cm³) and added to the above solution. The cross-linking reaction was left overnight, the resultant particles washed by tangential flow filtration (TFF) and recovered by lyophilisation (yield 0.93 g).

EXAMPLE 7

Preparation of Cross-linked Self-assembled Microparticles

Sebacic acid (0.619 g, 6.12 mmol) and NMM (0.62 g, 6.12 mmol) were dissolved in water (10 cm³) and a sample placed on a microscope. Almost monodispersed spherical entities of ~2.5 µm diameter were observed.
Poly-epsilon-lysine (PeK) (1 g, 5.83 mmol of $NH_2$) was dissolved in water (10 cm³) and added to the above solution of Sebacic acid/NMM microspheres. The mixture was filtered through a 0.45 µm membrane and a sample placed on a microscope. Microspheres of ~2.5 µm diameter were still present. This solution was diluted with water to 50 cm³. EDCI (2.24 g, 11.7 mmol) and HONSu (2.0 g, 17.4 mmol) were dissolved in water (10 cm³) and added to the above solution. The cross-linking reaction was left overnight, the resultant particles washed by TFF and recovered by lyophilisation.

EXAMPLE 8

Preparation of Cross-linked Self-assembled Microparticles

Sebacic acid (5.06 g, 25 mmol) and imidazole (3.4 g, 50 mmol) were dissolved in water (50 cm³) and a sample placed on a microscope. Almost monodispersed spherical entities of ~2.5 µm diameter were observed.
Poly-epsilon-lysine (PeK) (8.576 g, 50 mmol of $NH_2$) was dissolved in water (50 cm³) and added to the above solution of Sebacic acid/imidazole microspheres. The mixture was filtered through a 0.45 µm membrane and a sample placed on a microscope. Microspheres of ~2.5 µm diameter were still present (FIG. 3). This solution was diluted with water to 500 cm³. EDCI (4.8 g, 25 mmol) was dissolved in water (20 cm³) and added to the above solution. The cross-linking reaction was left for 1 h then a further 25 mmol of EDCI added before leaving overnight. The resultant particles washed with water by decantation and recovered by lyophilisation (FIG. 4).

EXAMPLE 9

Preparation of Cross-linked Self-assembled Microparticles

Sebacic acid (5 g, 24.7 mmol) and (3-Aminopropyl) trimethoxysilane (8.42 g, 46.9 mmol) were dissolved in water (50 cm³) and a sample placed on a microscope. Almost monodispersed spherical entities of ~2.5 µm diameter were observed.
The mixture was left overnight then acidified with concentrated hydrochloric acid. The addition of hydrochloric acid led to the formation of silica within the particles creating a Sebacic acid/silica composite.

EXAMPLE 10

Preparation of Cross-linked Self-assembled Microparticles

Sebacic acid (5 g, 24.7 mmol) and N-[3-(Trimethoxysilyl)propyl]ethylenediamine (5.77 g, 51.9 mmol of amine) were dissolved in water (50 cm$^3$) and a sample placed on a microscope. Almost monodispersed spherical entities of ~2.5 μm diameter were observed.

This solution was diluted with water to 500 cm$^3$. EDCI (20 g, 104 mmol) was dissolved in water (100 cm$^3$) and added to the above solution. The mixture was left overnight then acidified with concentrated hydrochloric acid. The addition of hydrochloric acid led to the formation of silica within the particles creating a Sebacic acid/silica composite.

EXAMPLE 11

Preparation of Cross-linked Self-assembled Microparticles

Sebacic acid (5 g, 24.7 mmol) and N1-(3-Trimethoxysilylpropyl)diethylenetriamine (4.37 g, 46.9 mmol of amine) were dissolved in water (50 cm$^3$) and a sample placed on a microscope. Almost monodispersed spherical entities of ~2.5 μm diameter were observed.

This solution was diluted with water to 500 cm$^3$. EDCI (20 g, 104 mmol) was dissolved in water (100 cm$^3$) and added to the above solution. The mixture was left overnight then acidified with concentrated hydrochloric acid. The addition of hydrochloric acid led to the formation of silica within the particles creating a Sebacic acid/silica composite.

EXAMPLE 12

Preparation of a Self-assembled Macroporous Cross-linked Sheet

Sebacic acid (0.619 g, 6.12 mmol) and NMM (0.62 g, 6.12 mmol) were dissolved in water (10 cm$^3$) and a sample placed on a microscope. Almost monodispersed spherical entities of ~2.5 μm diameter were observed.

Poly-epsilon-lysine (PeK) (1 g, 5.83 mmol of NH$_2$) was dissolved in water (10 cm$^3$) and added to the above solution of Sebacic acid/NMM microspheres. The mixture was filtered through a 0.45 μm membrane and a sample placed on a microscope. Microspheres of ~2.5 μm diameter were still present. EDCI (2.24 g, 11.7 mmol) and HONSu (2.0 g, 17.4 mmol) were dissolved in water (10 cm$^3$) and added to the above solution. The cross-linking reaction was left overnight, the resultant sheets washed with water and dried by lyophilisation. The SEM shown in FIG. 5 clearly demonstrates the fused microsphere structure of the macroporous polymer formed.

EXAMPLE 13

Preparation of a Self-assembled Macroporous Cross-linked Sheet (12-Phosphonododecyl)phosphonic acid (330 mg, 1 mmol) and NMM (404 mg, 4 mmol were dissolved in water. A sample placed on a microscope confirmed the presence of virtually monodispersed microspheres. PeK (343 mg, 2 mmol NH$_2$) was dissolved in water (10 cm$^3$) and added to the bis-phosphonic acid solution prepared above. Microspheres were still present at this stage. EDCI (1.15 g, 6 mmol) dissolved in water (10 cm$^3$) was added and the mixture immediately poured into a tray. Again microspheres were still present at this stage. A sheet formed after ~2 h which was washed thoroughly with water. The final sheet had a rubbery texture.

EXAMPLE 14

The self-assembled microparticles and macroporous cross-linked sheets of Examples 1 to 13 were all suitable for use in personal care products and in home care products according to the invention. The microparticles may be used to replace microplastics in known home care and personal care compositions. The products according to the invention have the benefit of containing microscale particles which do not contain non-biodegradable microplastics but have functionality provided by the presence of microparticles whilst being biodegradable.

EXAMPLE 15

Biocide Formulations

Biocides for personal care, cosmetics, home care and general disinfection are currently limited by the time they stay in contact with the surface to be treated due to abrasion. For example, surface sprays of the type used for disinfection in hospitals have a limited active lifetime and consequently reduced activity against hospital infections such as MRSA, *p.auregenosa* and *c.difficile*. In addition, some surface sprays contain organic solvents such as isopropanol or non-biodegradable components such as silicone oils to reduce abrasive removal of the biocides.

Cationic and amphoteric biocides such as quaternary ammonium compounds act against pathogens by solubilising the cell membrane, resulting in cell lysis and death. There are many biocides used commercially for disinfection which include chlorhexidine, benzalkonium chloride, climbazole, didecyldimethylammonium chloride, dodecyldipropylenetriamine, which are cationic compounds. Additionally some biocides are polymeric cationic compounds such as Poly(diallyldimethylammonium chloride). These compounds can be readily formulated into spherical microparticles using the technology described herein, which will allow for reduced abrasive removal on surfaces, skin and hair; potentially allowing for controlled release of the biocide. Additionally, biocides containing multiple cationic compounds in the same microparticle are possible and may provide formulations that can be tailored and targeted to specific applications where the source of infection is well defined.

Figure 8:
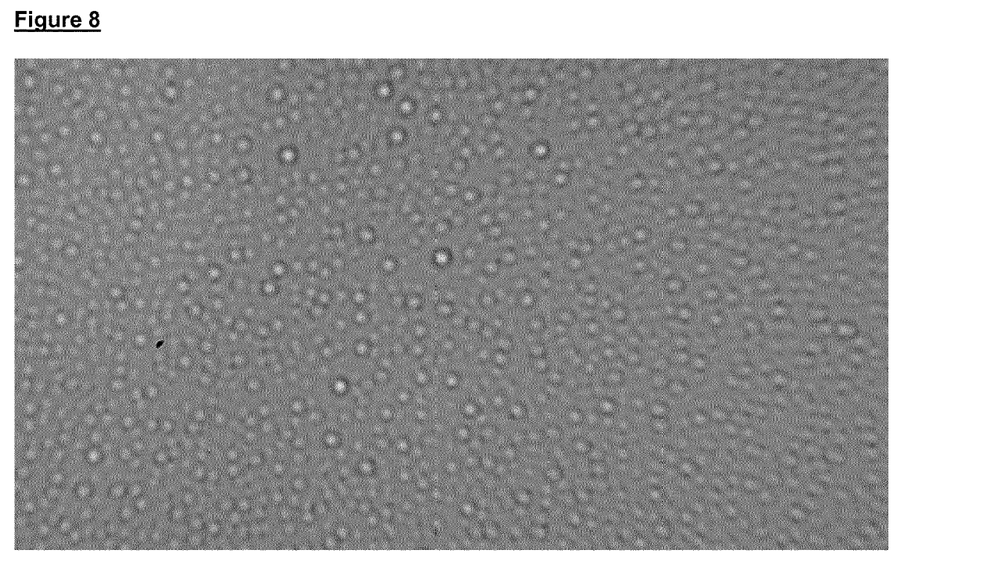

The samples produced were as follows:
Poly(diallyldimethylammonium chloride) (PDAC) Spherisomes PDAC (1.615 g, 10 mmol) was dissolved in water (50 cm$^3$) and NaOH (0.4 g, 10 mmol) added. Brassylic acid (1.22 g, 5 mmol) was added to this solution and allowed to dissolve overnight. This appeared to be a clear solution but was confirmed to be a suspension of ~3 μm microparticles and a novel formulation of PDAC when observed under the microscope and the results are shown in FIG. 8 shows PDAC-Brassylic acid microparticle formulation.
Didecyldimethylammonium chloride (DDAC)

DDAC (9.04 cm$^3$ of 40% w/v solution, 10 mmol) was diluted with water to 50 cm$^3$ and NaOH (0.4 g, 10 mmol) added. Brassylic acid (1.22 g, 5 mmol) was added to this solution and allowed to dissolve overnight. This appeared to be a hazy solution but was confirmed to be a suspension of ~3 μm microparticles and a novel formulation of DDAC when observed under the microscope.

Dodecyldipropylenetriamine (DDPT)

DDPT (9.97 cm$^3$ of 30% w/v solution, 10 mmol) was diluted with water to 50 cm$^3$ and Brassylic acid (3.66 g, 15 mmol) was added to this solution and allowed to dissolve overnight. This appeared to be a clear solution but was confirmed to be a suspension of ~3 μm microparticles and a novel formulation of DDPT when observed under the microscope.

EXAMPLE 16

Antimicrobial Macroporous Sheets

The hydrophilic nature of the porous polymer formed by collision of the biscarboxy fatty acid microparticles is advantageous in for absorbent sheets. When the biscarboxy fatty acids are combined with poly-ε-lysine and cross-linked to form such a porous matrix the natural antimicrobial activity of the components of the wound dressing can be retained and enhanced when necessary. In cationic form, where there is an excess of poly-ε-lysine over the fatty acids the materials have been shown to retain the characteristics of the food preservative providing novel antimicrobial sheets. The porous nature of the material will allow for improved moisture retention combined with a cationic nature capable of destroying microbial biofilms.

The anti-biofilm capability of a cationic sheet was assessed using a mixed microbial species CDC reactor model. The product of Example 13 was employed in these experiments.

Two mixed species biofilms were prepared as shown below and tested against PBS and a control anionic dressing.

Multi Species Biofilm 1
*Staphylococcus aureus* NCTC 8325
*Pseudomonas aeruginosa* NCIMB 10434
*Acinetobacter baumannii* ATCC 19606
*Staphylococcus epidermidis*
Multi Species Biofilm 2
*Staphylococcus aureus* NCTC 8325
MRSA
VRE *faecalis* NCTC 12201
*Candida albicans* ATCC MYA-2876 SC5313
*Escherichia coli* NCTC 12923 Page 3 of 6 DOT 202 (03)
Preparation of Mixed Inoculum 1

Twenty-four hour cultures of *Staphylococcus aureus, Pseudomonas aeruginosa, Acinetobacter baumannii*, and *Staphylococcus epidermidis* were harvested from appropriate agar plate using a sterile swab and suspended in 20 cm$^3$ of Tryptone Soya Broth (TSB). The mixed species suspension was diluted in TSB to give an overall concentration of 107±5×106 cfuml−1 and used as the inoculum for the CDC reactor. The CDC reactor was incubated for 72 hours at 37° C. with shaking at 50 rpm in order to encourage biofilm growth.

Preparation of Mixed Inoculum 2

Twenty-four hour cultures of *Staphylococcus aureus,* Methicillin-resistant *staphylococcus aureus,* Vancomycin-resistant *Enterococcus, Candida albicans* and *Escherichia coli* were harvested from appropriate agar plate using a sterile swab and suspended in 20 cm$^3$ of TSB. The mixed species suspension was diluted in TSB to give an overall concentration of 107±5×106 cfuml−1 and used as the inoculum for the CDC reactor. The CDC reactor was incubated for 72 hours at 37° C. with shaking at 50 rpm in order to encourage biofilm growth.

Biofilm Treatment

After incubation the test coupons were removed from the CDC reactor and washed 3 times in sterile phosphate buffered saline (PBS) in order to remove planktonic cells. The washed coupons were then treated by sandwiching the coupon between two discs of the wound dressing material. The dressings were activated prior to testing by the addition of 400 mm$^3$ PBS+1% TSB to each disc. Control coupons were submerged in 1 cm$^3$ of PBS +1% TSB. All samples were tested in triplicate. Following the 24 hour treatment period, the coupons were placed in 1 cm$^3$ PBS and sonicated for 15 minutes in order to recover any viable microorganisms attached to the coupons. Recovered microorganisms were quantified using serial dilutions and spread plates.

Mixed Inoculum 1

Figure 9:
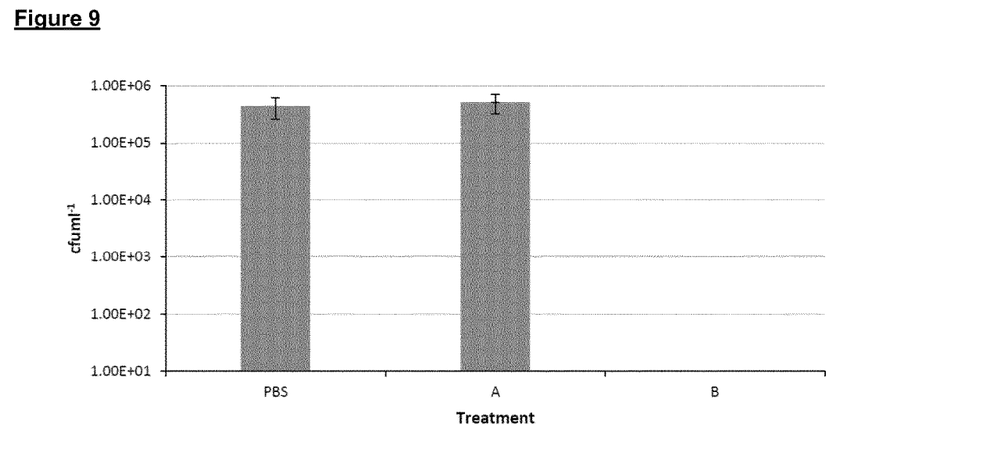
Figure 10:
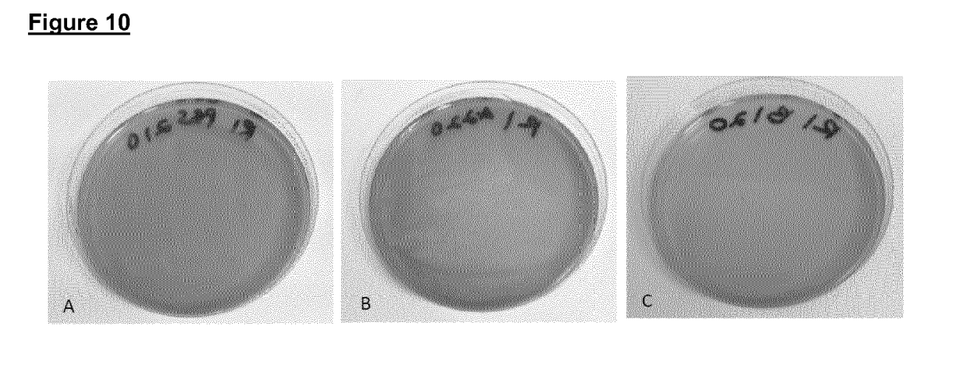

Following treatment with the control dressing (A), bacterial recovery was similar to PBS only treatment controls as shown in FIG. 9. No viable organisms were recovered from coupons treated with cationic dressing (B). This represents a greater than 5 log reduction compared to PBS treated controls. The surviving organism post treatment were predominantly *Pseudomonas aeruginosa* (FIG. 10).

Mixed Inoculum 2

Figure 11:
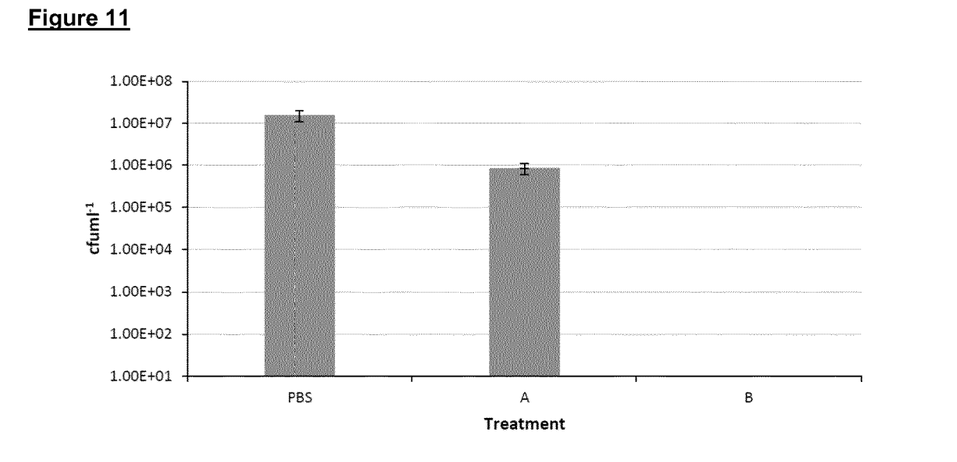
Figure 12:
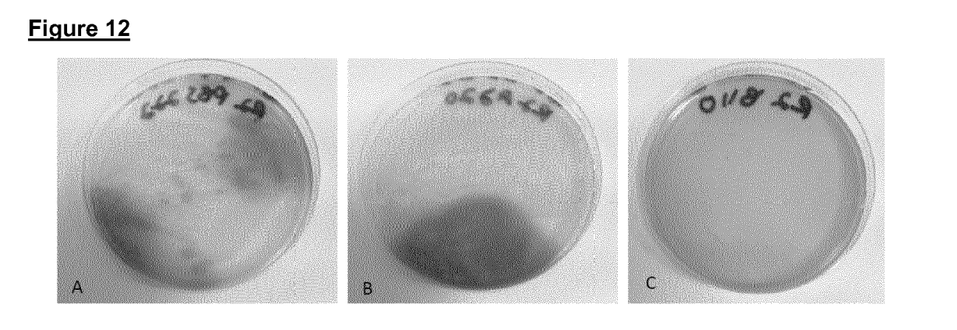

Treatment with control dressing (A) resulted in a 1.27 log reduction in the number of viable bacteria recovered compared to the PBS treated controls. No viable organisms were recovered from coupons treated with cationic dressing (B). This represents a greater than 7 log reduction compared to the PBS treated controls (FIG. 11). Surviving organisms were mixed species (FIG. 12).

The invention claimed is:

1. A personal care product or a home care product comprising a base composition and a particulate component comprising a self-assembled microparticle having a particle size of 0.5 to 10 microns which comprises an acid having two or more acid groups comprising one or more of brassylic acid, sebacic acid and/or azelaic acid and an organic base comprising one or more of N-methylmorpholine,N,N-dimethylaminoethanol, 4-dimethylaminopyridine, imidazole, 1-methylamidazole poly(diallyldimethylammonium chloride) (PDAC), didecyldimethylammonium chloride (DDAC), dodecyldipropylenetriamine (DDPT) and poly epsilon lysine;
   wherein the personal care product or home care product further comprises a base composition selected from a detergent composition, a fabric softener a fragrance and a dishwashing composition, if a home care product, and selected from a skin cream, cosmetic, fragrance, deodorant, hand or face wipe, hand wash, hand scrub, shampoo, conditioner, mouth wash and tooth paste, if a personal care product.

2. A personal care product or a home care product according to claim 1 in which the microparticle has a particle size of 1 to 5 microns.

3. A personal care product or a home care product according to claim 1 in which the molar ratio of acid groups to basic groups in the acid and base is from 0.6 to 1.4:1.

4. A personal care product or a home care product according to claim 1 in which the microparticle comprises acid groups and basic groups in a molar ratio from 0.7 to 1.3:1.

5. A personal care product or a home care product according to claim 1 in which the microparticle comprises a self-assembled microparticle obtainable by a process comprising contacting the acid and organic base in a hydrophilic solvent, wherein the acid is insoluble or sparingly soluble in the hydrophilic solvent and the organic base is soluble in a hydrophilic solvent.

6. A personal care product or a home care product according to claim 5 in which the solvent comprises an aqueous solution.

7. A personal care product or a home care product according to claim 1 in which the microparticle further comprises a bis acid of general formula $HOOC-(CH_2)_n-COOH$ wherein n is sufficiently large that the bis acid is sparingly soluble or insoluble in water.

* * * * *